(12) United States Patent
Qian

(10) Patent No.: US 8,162,665 B2
(45) Date of Patent: Apr. 24, 2012

(54) SINGLE-PART, LIGHT-CURABLE, SELF-ADHERING DENTAL RESTORATIVE COMPOSITION AND METHOD OF USING THE SAME

(75) Inventor: Xuejun Qian, Foothill Ranch, CA (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 13/110,253

(22) Filed: May 18, 2011

(65) Prior Publication Data

US 2011/0217677 A1  Sep. 8, 2011

Related U.S. Application Data

(63) Continuation of application No. 12/190,762, filed on Aug. 13, 2008, now Pat. No. 7,946,850.

(51) Int. Cl.
*A61C 5/00* (2006.01)
*A61K 6/083* (2006.01)
*A61K 6/08* (2006.01)
*C08F 2/50* (2006.01)

(52) U.S. Cl. ....... 433/228.1; 522/83; 522/115; 522/171; 523/115; 523/116; 523/117

(58) Field of Classification Search .................. 522/77, 522/81, 83, 171, 115; 523/115–117; 433/228.1
See application file for complete search history.

(56) References Cited

U.S. PATENT DOCUMENTS

| | | | |
|---|---|---|---|
| 4,362,842 A * | 12/1982 | Masuhara et al. | 524/854 |
| 4,539,382 A * | 9/1985 | Omura et al. | 526/276 |
| 4,775,585 A | 10/1988 | Hagiwara et al. | |
| 4,792,632 A | 12/1988 | Ellrich et al. | |
| 4,911,899 A | 3/1990 | Hagiwara et al. | |
| 5,367,002 A | 11/1994 | Huang et al. | |
| 6,121,344 A * | 9/2000 | Angeletakis et al. | 523/116 |
| 6,211,264 B1 | 4/2001 | Lu et al. | |
| 6,309,221 B1 * | 10/2001 | Jensen | 433/226 |
| 6,359,090 B1 | 3/2002 | Angeletakis | |
| 6,593,395 B2 * | 7/2003 | Angeletakis et al. | 523/115 |
| 6,710,149 B2 * | 3/2004 | Moszner et al. | 526/278 |
| 6,811,400 B2 * | 11/2004 | Jensen et al. | 433/224 |
| 6,837,712 B2 | 1/2005 | Qian | |
| 6,890,968 B2 * | 5/2005 | Angeletakis et al. | 523/115 |
| 7,166,651 B2 | 1/2007 | Qian | |
| 7,214,726 B2 * | 5/2007 | Qian | 523/116 |
| 7,678,843 B2 * | 3/2010 | Fusejima et al. | 523/117 |
| 7,767,731 B2 * | 8/2010 | Chen et al. | 523/118 |
| 7,963,769 B2 * | 6/2011 | Qian | 433/228.1 |
| 7,968,618 B2 * | 6/2011 | Chen et al. | 523/118 |
| 2004/0110864 A1 * | 6/2004 | Hecht et al. | 523/113 |
| 2004/0235981 A1 * | 11/2004 | Qian | 523/115 |
| 2005/0014861 A1 * | 1/2005 | Qian | 523/116 |
| 2006/0004122 A1 * | 1/2006 | Hecht et al. | 523/115 |
| 2007/0197683 A1 | 8/2007 | Jia et al. | |
| 2007/0248927 A1 | 10/2007 | Luchterhandt et al. | |

* cited by examiner

*Primary Examiner* — Susan W Berman

(74) *Attorney, Agent, or Firm* — Wood, Herron & Evans, LLP

(57) ABSTRACT

A dental restorative composition comprises: (A) polymerizable monomer(s) selected from hydroxyethyl (meth)acrylate phosphate, hydroxypropyl (meth)acrylate phosphate, hydroxybutyl (meth)acrylate phosphate, dipentaerythritol penta(meth)acrylate phosphate, pentaerythritol tri(meth)acrylate phosphate, phenyl (meth)acryloxyethyl phosphate, and a combination thereof; (B) polymerizable monomer(s) having a molecular weight of 100-250, at least one hydroxyl group, and at least one ethylenically unsaturated group; (C) polymerizable monomer(s) having a molecular weight of 270-900, at least two ethylenically unsaturated groups and no acidic functional group; (D) photo-initiator(s); and (E) filler(s) each having a mean particle size of more than 0.005 microns and less than 70 microns. The weight ratio of (A+B):(C) ranges from 30:70 to 90:10, and the composition has a shear bond strength of at least 10MPa to both dentin and enamel after being light-cured.

23 Claims, No Drawings

SINGLE-PART, LIGHT-CURABLE, SELF-ADHERING DENTAL RESTORATIVE COMPOSITION AND METHOD OF USING THE SAME

CROSS REFERENCE TO RELATED APPLICATION

This application is a continuation of co-pending U.S. patent application Ser. No. 12/190,762 filed Aug. 13, 2008 and entitled SINGLE-PART, LIGHT-CURABLE, SELF-ADHERING DENTAL RESTORATIVE COMPOSITION AND METHOD OF USING THE SAME, the disclosure of which is incorporated herein by reference in its entirety as if completely set forth herein below.

FIELD OF INVENTION

This invention relates to a single-part, light-curable, self-adhering dental composition and a simplified method for filling a dental cavity with this single-part, light-curable, self-adhering dental restorative composition.

BACKGROUND OF INVENTION

There are several choices available as a filling material for filling a dental cavity: a traditional amalgam (a silver-mercury alloy), a glass ionomer, and a composite resin. In the past two decades, composite resin filling material has become the material of choice for dentists for filling dental cavities due to their exceptional esthetic properties, i.e. precise color-matching capability and excellent translucency. However, current composite resins generally do not have a self-adhesive property and generally require pre-treating the tooth structure (or tooth cavity wall) with an adhesive to bond the composite to the tooth structure. For some adhesives, an etchant and/or a primer are needed to etch and/or condition the tooth structure prior to adhesive application. For a $4^{th}$ generation dental adhesive system, such as OptiBond® FL (Kerr Corporation, Orange, Calif.), the restorative procedures would include the following steps: (1) remove carious dentition (dentin and enamel); (2) etch the cavity wall with a 37% Phosphoric Acid Gel Etchant (Kerr Corporation, Orange, Calif.); (3) rinse the etchant off the cavity wall with water; (4) briefly dry the cavity wall with compressed air using a dental air-syringe; (5) apply a layer of OptiBond® FL Primer (Kerr Corporation, Orange, Calif.) to the cavity wall; (6) evaporate the solvent within the primer with compressed air using a dental syringe; (7) apply a layer of OptiBond® FL Adhesive (Kerr Corporation, Orange, Calif.) to the primer-coated cavity wall; (8) air-thin the adhesive with compressed air; (9) light-cure the adhesive with a dental curing light; (10) place a composite resin filling material, such as Premise™ (Kerr Corporation, Orange, Calif.), either in bulk (or single increment) or in several increments; (11) light-cure the composite resin of each increment; and (12) remove excess composite resin and polish the restoration. Because of the many components and steps involved with the current dental cavity filling procedure using a composite resin filling material, the restorative procedure is quite complicated and time-consuming. Also, the procedure could be quite technique-sensitive as each specific adhesive has its own unique application procedure and care has to be given for each step for ensure a successful restoration. In addition, because of the many materials and steps involved, there will be increased chances for mistakes (i.e. using the wrong material or sequence of materials) and also contaminations due to saliva or blood during the procedure.

Recent development in the adhesive arena has simplified the restorative procedure to some extent with the introduction of various new primer and/or adhesive configurations: total-etch priming adhesive (the primer and adhesive are combined into a single part), self-etch primer (the etchant and primer are combined into a single part), and a self-etch adhesive (the etchant, primer and adhesive are combined into a single part). Nevertheless, an adhesive or an adhesive in combination with either an etchant or a self-etch primer is still needed to bond the composite resin filling material to the cavity wall.

It is highly desirable to further simplify the cavity-filling restorative procedure by imparting self-adhesiveness to the composite resin filling material and therefore eliminate the need for an etchant and an adhesive. To formulate a self-adhesive composite resin, adhesive monomers need to be incorporated into composite resin to provide an adhesive property to the composite resin. However, most adhesive monomers have high polymerization shrinkage due to their low molecular weight. The adhesive monomers generally have a high viscosity and tend to limit the amount of inorganic fillers that can be incorporated into the composite resin, resulting in more polymerization shrinkage. Therefore, a self-adhering composite resin incorporating adhesive monomers is expected to have excessive polymerization shrinkage upon light-curing, exerting excessive shrinkage force at the bonding interface between the composite resin filling material and the cavity wall. The excessive shrinkage force can cause debonding and therefore microleakage at the bonding interface, leading to secondary caries later on. Another potential issue with a self-adhering composite resin filling material is that the material is expected to be quite sticky due to the incorporation of adhesive monomers and can further compromise the bonding interface due to excessive stickiness. Another issue with a self-adhering composite resin filling material is that the adhesiveness of the material would be compromised due to much increased filler loading and therefore viscosity, making it difficult to effectively wet the tooth surface to establish a reliable bond without the help of an etchant and/or an adhesive. For those reasons or issues, there is still no viable commercialization of a truly self-adhering composite resin filling material that would eliminate the need for an etchant and/or an adhesive.

SUMMARY OF THE INVENTION

The current invention discloses a single-part, light-curable, self-adhering dental restorative composition consisting essentially of: (A) one or more first polymerizable monomers selected from the group consisting of hydroxyethyl (meth) acrylate phosphate, hydroxypropyl (meth)acrylate phosphate, hydroxybutyl (meth)acrylate phosphate, dipentaerythritol penta(meth)acrylate phosphate, pentaerythritol tri (meth)acrylate phosphate, phenyl (meth)acryloxyethyl phosphate, and a combination thereof, (B) one or more second polymerizable monomers having a molecular weight of 100-250, at least one hydroxyl group, and at least one ethylenically unsaturated group; (C) one or more third polymerizable monomers having a molecular weight of 270-900, at least two ethylenically unsaturated groups and no acidic functional group; (D) at least one photo-initiator; (E) one or more fillers each having a mean particle size of more than 0.005 microns and less than 70 microns, and (F) one or more optional ingredients selected from colorants, stabilizers, UV absorbers, solvents, fluoride-releasing compounds, antimicrobial additives, and surfactants, wherein the weight ratio of (A+B):(C) ranges from 30:70 to 90:10. The composition has a shear bond strength of at least 10 MPa to both dentin and enamel after being light-cured. In one embodiment, component (A) further comprises glyceryldi(meth)acrylate phosphate, bis{hydroxyethyl (meth)acrylate} phosphate, or a combination thereof. In another embodiment, the concentration of component (A) in the restorative composition, excluding fillers, is in the range of 10-50% by weight, and the concentration of component (B) in the restorative composition, excluding fillers, is in the range of 15-60% by weight.

The invention also discloses a restorative method for filling a dental cavity with the above self-adhering dental composition without first treating the dental cavity with an etchant, a primer and/or an adhesive. The omission of the steps of treating the dental cavity with an etchant, a primer and an adhesive significantly simplifies the restorative procedure, resulting in significant time savings for the dentist.

DETAILED DESCRIPTION OF THE INVENTION

The current invention discloses a single-part, light-curable, self-adhering dental restorative composition and a simplified restorative method for filling a dental cavity with the self-adhering dental composition without first treating the dental cavity with an etchant, a primer and/or an adhesive. One benefit of the inventive self-adhering composition is its excellent bond strength to tooth structure (both dentin and enamel) without the need for an etchant, a primer and/or an adhesive. The excellent adhesion can reduce the chance of de-bonding due to polymerization shrinkage of the material during polymerization and subsequent microleakage. Another benefit of the inventive self-adhering composition is its excellent mechanical property, providing a restorative material that is strong and durable. Yet another benefit of the inventive self-adhering composition is its increased filler loading and therefore reduced shrinkage while maintaining a desirable viscosity of the composition, thereby leading to reduced microleakage. Yet another benefit of the inventive self-adhering composition is its reduced stickiness and therefore improved handling property, thereby leading to reduced microleakage and contributing to long-term success of the restoration.

In accordance with an embodiment of the invention, the single-part, light-curable, self-adhering dental restorative composition comprises: (A) one or more first polymerizable monomers having at least one phosphorus-containing acidic moiety and at least one ethylenically unsaturated group; (B) one or more second polymerizable monomers having a molecular weight of 100-250, at least one hydroxyl group, and at least one ethylenically unsaturated group; (C) one or more third polymerizable monomers having a molecular weight of 270-900, at least two ethylenically unsaturated groups and no acidic functional group; (D) at least one photoinitiator; and (E) one or more fillers each having a mean particle size of more than 0.005 microns and less than 70 microns. The weight ratio of (A+B):(C) ranges from 30:70 to 90:10, the concentration of component (A) in the restorative composition, excluding fillers, is in the range of 10-50% by weight, the concentration of component (B) in the restorative composition, excluding fillers, is in the range of 15-60% by weight, and the composition has a shear bond strength of at least 10 MPa to both dentin and enamel.

The first polymerizable monomer (A) has at least one phosphorus-containing acidic moiety and at least one ethylenically unsaturated group. Examples of ethylenically unsaturated groups include, but are not limited to, acrylate, methacrylate, acrylamide, methacrylamide, and/or vinyl groups. Examples of phosphorus-containing acidic moieties include, but are not limited to, a phosphoric acid group, a phosphonic acid group, bisphosphonic acid group, a phosphoric acid derivative, a phosphonic acid derivative, and/or a bisphosphonic acid derivative, with a derivative being a salt or ester of the respective acid. Component (A) can be one or a mixture of polymerizable monomers having at least one phosphorus-containing acidic moiety and at least one ethylenically unsaturated group. Examples of polymerizable monomers having at least one phosphorus-containing acidic moiety and at least one ethylenically unsaturated group include, but are not limited to, hydroxyethyl(meth)acrylate phosphate {(meth)acrylate=methacrylate or acrylate}, hydroxypropyl(meth)acrylate phosphate, hydroxybutyl (meth)acrylate phosphate, hydroxyhexyl(meth)acrylate phosphate, hydroxyoctyl(meth)acrylate phosphate, hydroxydecyl(meth)acrylate phosphate, glyceryldi(meth)acrylate phosphate, dipentaerythritol penta(meth)acrylate phosphate, pentaerythritol tri(meth)acrylate phosphate, phenyl (meth)acryloxyethyl phosphate, and bis {hydroxyethyl(meth)acrylate} phosphate, or combinations thereof. In one embodiment, the first polymerizable monomer (A) has at least one phosphorus-containing acidic moiety and at least two ethylenically unsaturated groups. Examples of polymerizable monomer having at least one phosphorus-containing acidic moiety and at least two ethylenically unsaturated group include, but are not limited to, glyceryldi(meth)acrylate phosphate, dipentaerythritol penta(meth)acrylate phosphate, pentaerythritol tri(meth)acrylate phosphate, and bis{hydroxyethyl(meth)acrylate} phosphate. In another embodiment, the first polymerizable monomer (A) is selected from the group consisting of glyceryldi(meth)acrylate phosphate, and bis{hydroxyethyl(meth)acrylate} phosphate, or mixtures thereof. In yet another embodiment, the first polymerizable monomer (A) is glyceryldi(meth)acrylate phosphate (also called "glyceryldimethacrylate dihydrogen phosphate"). The concentration of component (A) in the restorative composition, excluding fillers, is in the range of 10-50% by weight. In one embodiment, the concentration of component (A) in the restorative composition, excluding fillers, is in the range of 15-40% by weight. In another embodiment, the concentration of component (A) in the restorative composition, excluding fillers, is in the range of 20-35% by weight.

The second polymerizable monomer (B) has a molecular weight of 100-250, at least one hydroxyl group, and at least one ethylenically unsaturated group. Component (B) can be one or a mixture of polymerizable monomers having a molecular weight of 100-250, at least one hydroxyl group, and at least one ethylenically unsaturated group. Examples of ethylenically unsaturated groups include, but are not limited to, acrylate, methacrylate, acrylamide, methacrylamide, and/or vinyl groups. Examples of polymerizable monomers having a molecular weight of 100-250, at least one hydroxyl group, and at least one ethylenically unsaturated group include, but are not limited to, the following: hydroxyethyl (meth)acrylate, hydroxypropyl (meth)acrylate, hydroxybutyl (meth)acrylate; glyceryl di(meth)acrylate, glyceryl mono (meth)acrylate, 2-hydroxyethoxyethyl (meth)acrylate, or combinations thereof. In one embodiment, the second polymerizable monomer (B) is selected from the group consisting of hydroxyethyl (meth)acrylate, hydroxypropyl (meth)acrylate, glycerol di(meth)acrylate, glycerol mono(meth)acrylate, and combinations thereof. The concentration of component (B) in the restorative composition, excluding fillers, is in the range of 15-60% by weight. In one embodiment, the concentration of component (B) in the restorative composition, excluding fillers, is in the range of 20-50% by weight.

The third polymerizable monomer (C) has a molecular weight of 270-900 and at least two ethylenically unsaturated groups and no acidic functional group. Component (C) can be one or a mixture of polymerizable monomers having a molecular weight of 270-900 and at least two ethylenically unsaturated groups. Examples of ethylenically unsaturated groups include, but are not limited to, acrylate, methacrylate, acrylamide, methacrylamide, and/or vinyl groups. Examples of polymerizable monomers having a molecular weight of 270-900 and at least two ethylenically unsaturated groups include, but are not limited to, the following: triethyleneglycol di(meth)acrylate (TEGDA or TEGDMA), tetraethyleneglycol di(meth)acrylate, polyethyleneglycol di-(meth)acrylate, polypropyleneglycol di-(meth)acrylate, polytetramethyleneglycol di-(meth)acrylate, trimethyloylpropane tri(meth)acrylate, ethoxylated trimethyloylpropane tri(meth)acrylate (ETMPT(M)A-nEO, n=total number of moles of ethylene oxide in the molecule, with n=3-15 being preferred), UDMA (reaction product of 2-hydroxyethyl methacrylate with 2,4,4 -trimethylhexane diisocyanate), ethoxylated bisphenol A di(meth)acrylate ("EBPAD(M)A-nEO", n=total number of moles of ethylene oxide in the molecule, with 2-15 being preferred), 2,2-bis[4-(2-hydroxy-3-methacryloylpropoxy)-phenyl]-propane (Bis-GMA), bisphenol A dimethacrylate. In one embodiment, component (C) is selected from the group consisting of TEGDMA, ETMPT(M)A-nEO(n=3-15), UDMA, EBPAD(M)A-nEO (n=2-12), and Bis-GMA, and combinations thereof.

For optimal adhesion and mechanical properties, the weight ratio of (A+B):(C) ranges from 30:70 to 90:10. With weight ratio of (A+B):(C)>90:10, the mechanical strength of cured composition will be too low to function as a restorative material. With weight ratio of (A+B):(C)<30:70, the bond strength of the restorative composition to tooth structure will be too low. In one embodiment, the weight ratio of (A+B):(C) ranges from 40:60 to 90:10. In another embodiment, the weight ratio of (A+B):(C) ranges from 45:55 to 75:25. In yet another embodiment, the weight ratio of (A+B):(C) ranges from 50:50 to 75:25. In still another embodiment, the weight ratio of (A+B):(C) ranges from 30:70 to 80:20.

The restorative composition can further optionally comprise other polymerizable monomer(s) having at least one ethylenically unsaturated group. Examples of optional polymerizable monomers include both monomers having no acidic moiety as well as monomers having one or more acidic moieties. Examples of optional polymerizable monomers include, but are not limited to, maleic acid, itaconic acid, methacrylic acid, acrylic acid, maleic anhydride, 4-methacryloxyethyltrimellitic anhydride, 4-methacryloxyethyltrimellitic acid, (meth)acrylated homopolymer or copolymer of an α, β-unsaturated carboxylic acid {e.g. (meth)acrylated poly(acrylic acid), (meth)acrylated poly(acrylic acid-maleic acid) copolymer and (meth)acrylated poly(acrylic-maleic acid-itaconic acid) copolymer}, any addition product of mono-/di-anhydride compound with a hydroxyalkylmethacrylate compound (e.g. the addition product of pyromellitic acid anhydride and glycerol dimethacrylate, the addition product of 3,3',4,4'-benzophenonetetracarboxylic dianhydride and hydroxyethyl methacrylate, the addition product of phthalic anhydride and hydroxyethyl methacrylate, and the addition product of maleic anhydride and glycerol dimethacrylate), methyl (meth)acrylate, ethyl (meth)acrylate, propyl (meth)acrylate, butyl (meth)acrylate, hexyl (meth)acrylate, octyl (meth)acrylate, lauryl (meth)acrylate, decyl (meth)acrylate, tridecyl (meth)acrylate, 2-ethoxyethyl (meth)acrylate, 2'-ethoxy-2-ethoxyethyl (meth)acrylate, ethyleneglycol di(meth)acrylate, diethyleneglycol di(meth)acrylate, polyethyleneglycol mono-(meth)acrylate, polypropyleneglycol mono-(meth)acrylate, polytetramethyleneglycol mono-(meth)acrylate, hexanediol di(meth)acrylate, tetrahydrofurfuryl (meth)acrylate, N,N'-methylenebis(acrylamide), N,N'-ethylenebis(acrylamide), and N,N'-butylenebis(acrylamide), or any mixture thereof.

The photoinitiator (D) can be any compound that can generate free radicals upon exposure to a light source and cause the polymerization or hardening of the composition. The light source can be any dental curing light that emits light in the visible or ultraviolet range. Examples of photoinitiators include, but are not limited to, diketone compounds, benzoin, benzoin ethers and esters, 2,2-diethoxy acetophenone, monoacylphosphine oxide, bisacylphosphine oxide as disclosed in U.S. Pat. No. 4,792,632, which is expressly incorporated by reference herein in its entirety, diaryliodonium salt, and triarylsulfonium salt, and any mixture of photoinitiators. Examples of diketone compounds include, but are not limited to, camphorquinone and 1-phenyl-1,2-propanedione. Additionally, a coinitiator can be used together with a photoinitiator to enhance curing efficiency. Coinitiators include tertiary amine and sulfinate compounds. Examples of coinitiators include, but are not limited to, ethyl 4-(N,N-dimethylamino) benzoate, 4-(N,N-dimethylamino) benzoic acid, 4-(N,N-dimethylamino) benzonitrile, 4-(N,N-dimethylamino) benzaldehyde, 2-(ethylhexyl)-4-(N,N-dimethylamino) benzoate, N,N-dimethylaminoethyl methacrylate, N,N-dimethylaminophenethyl alcohol, sodium benzenesulfinate, and sodium toluenesulfinate. In one embodiment, a photoinitiator system includes the combination of camphorquinone and a tertiary amine. Examples of tertiary amines include, but are not limited to, ethyl 4-(N,N-dimethylamino) benzoate, 4-(N,N-dimethylamino) benzoic acid, 4-(N,N-dimethylamino) benzonitrile, 4-(N,N-dimethylamino) benzaldehyde, 2-(ethylhexyl)-4-(N,N-dimethylamino) benzoate, N,N-dimethylaminoethyl methacrylate, and N,N-dimethylaminophenethyl alcohol. In another embodiment, a photoinitiator system includes the combination of camphorquinone and bisacylphosphine oxide or monoacylphosphine oxide. In another embodiment, a photoinitiator system includes the combination of camphorquinone, tertiary amine, and bisacylphosphine oxide or monoacylphosphine oxide. In one embodiment, a photoinitiator may be present at a concentration of 0.01% (w/w) to about 10% (w/w) of the composition. In another embodiment, a photoinitiator may be present at a concentration of 0.05% (w/w) to about 5% (w/w) of the composition.

The filler (E) can be any one or more fillers that have a mean particle size of more than 0.005 microns and less than 70 microns. The mean particle size is measured by a particle size measurement instrument employing laser light scattering methodology. An example of such instrument is a Horiba Model 910 Laser Scattering Particle Size Analyzer (Horiba Inc, Irvine, Calif.). Filler (E) is selected from group consisting of metal, inorganic salt, oxide, fluoride, silicate glass, aluminosilicate glass, aluminoborosilicate glass, fluoroaluminosilicate glass, quartz, silica, zirconia-silica, and polymeric filler. In one embodiment, inorganic fillers for increased x-ray contrast ability include metals, salts, oxides, fluorides, silicate glass, aluminosilicate glass, aluminoborosilicate glass, and fluoroaluminosilicate glass containing elements of high atomic number such as Sr, Y, Zr, Ba, La, Hf, Zn, Bi, W, rare earth metals, and combinations of these. Examples include barium sulfate, silver, strontium fluoride, barium fluoride, ytterbium fluoride, yttrium fluoride, barium tungstate, zinc oxide, zirconium oxide, bismuth(III) oxide, bariumaluminosilicate, bariumaluminoborosilicate, strontiumaluminosilicate, bariumfluoroaluminosilicate, strontiumfluoroaluminosilicate, strontiumzincfluoroaluminosilicate, zincaluminosilicate, zirconiumsilicate, etc. Useful silicas include fumed silica, colloidal silica, and/or precipitated silica. Examples of silicas include Aerosil® series such as OX-50, OX-130, and OX-200 silica sold by Degussa (Ridgefield Park, N.J.), and Cab-O-Sil® M5 and Cab-O-Sil® TS-530 silica sold by Cabot Corp (Tuscola, Ill.). The filler also includes nanoparticles such as those obtained through a sol-gel process. Useful nanoparticles include, but are not limited to, silica, aluminum oxide, zinc oxide, zirconium oxide, zirconium silicate, zirconia/silica, ytterbium fluoride, yttrium fluoride, aluminosilicate, aluminoborosilicate, fluoroaluminosilicate, or mixtures thereof. Mixtures of different fillers can be used. For inorganic fillers, the surface of the filler may be treated or coated with a coupling agent to enhance the interfacial bonding between the filler and resin matrix and improve mechanical properties. One useful example of a coupling agent is gamma-methacryloyloxypropyltrimethoxy-silane (MPTMS). In one embodiment, the one or more fillers in filler component (E) are non-reactive towards the acidic polymerizable monomers of component (A).

In one embodiment, for optimized filler loading, mechanical property, polymerization shrinkage, stability, and adhesive property of the composition, the inventive restorative composition comprises three fillers of different particle sizes.

For the first filler (E1), at least one filler having a mean particle size of more than 4.5 microns and less than 70 microns can be used. In one embodiment, the first filler has a mean particle size of more than 5 microns. In another embodiment, the first filler has a mean particle size of more than 10 microns. In yet another embodiment, the first filler has a mean particle size of more than 20 microns.

For the second filler (E2), at least one filler having a mean particle size of more than 0.25 microns, but no more than 4.5 microns can be used. In one embodiment, the second filler has a mean particle size of 0.3-3.0 microns. In another embodiment, the second filler has a mean particle size of 0.3-2.0 microns.

For the third filler (E3), at least one filler having a mean particle size of 0.005-0.25 micron can be used. In one embodiment, the third filler has a mean particle size of 0.01-0.20 microns.

Components (E1), (E2), and (E3) are independently selected from the fillers described above for filler (E).

According to one embodiment, the first filler (E1) is a polymeric filler comprising 5-100% by weight of polymeric matrix and 0-95% by weight of at least one inorganic filler. In one embodiment, the polymeric filler comprises 10-50% by weight of polymeric matrix and 50-90% by weight of at least one inorganic filler. In another embodiment, the polymeric filler comprises 10-30% by weight of polymeric matrix and 70-90% by weight of at least one inorganic filler. In one embodiment, the polymeric matrix comprises one or more thermoset materials. Examples of thermoset materials include, but are not limited to, crosslinked epoxy(ies), crosslinked (meth)acrylate(s), crosslinked polyester(s), and crosslinked polyimide(s), or any mixture thereof. In one embodiment, the thermoset material is a crosslinked (meth)acrylate(s). The crosslinked (meth)acrylate(s) is obtained by polymerizing one or a mixture of (meth)acrylate monomers comprising at least one (meth)acrylate monomer having at least two (meth)acrylate functional groups. Any of the (meth)acrylate monomers discussed in previous paragraphs that has at least two (meth)acrylate functional groups can be used.

As an example, the polymeric filler for first filler (E1) can be obtained by the following procedure. First, a homogenous mixture comprising at least one crosslinkable monomer(s) and optionally a curing initiator is obtained. The curing initiator can be a photoinitiator, a heat initiator, and/or a redox initiator. Next, the crosslinkable monomer mixture is either directly polymerized or homogeneously blended with one or more inorganic fillers and then polymerized. The means of polymerization can be by light, by heat, and/or by redox initiator. The polymerized material is then ground into fine particles with a mean particle size of more than 4.5 microns and less than 70 microns. In one embodiment, the polymeric filler has a mean particle size of more than 5 microns. In another embodiment, the polymeric filler has a mean particle size of more than 10 microns and less than 60 microns. In another embodiment, the polymeric filler has a mean particle size of more than 20 microns and less than 50 microns. Examples of suitable inorganic fillers for incorporation into the polymeric matrix include, but are not limited to, the fillers described above for filler (E).

In one embodiment, the mean particle size of the inorganic fillers incorporated within the polymeric fillers is in the range of 0.005-20 microns. In another embodiment, the mean particle size of the inorganic fillers incorporated within the polymeric fillers is in the range of 0.01-4.5 microns. In yet another embodiment, the mean particle size of the inorganic fillers incorporated within the polymeric fillers is in the range of 0.01-2.0 microns. In one embodiment, the polymeric filler comprises 10-50% by weight of the crosslinked methacrylate(s) matrix and 50-90% by weight of one or more inorganic fillers having a mean particle size in the range of 0.01-4.5 microns, and the polymeric filler has a mean particle size of 10-60 microns. In another embodiment, the polymeric filler comprises 10-30% by weight of the crosslinked methacrylate(s) matrix and 70-90% by weight of one or more inorganic fillers having a mean particle size in the range of 0.01-2.0 microns, and the polymeric filler has a mean particle size of 10-60 microns. In another embodiment, the polymeric filler comprises 10-30% by weight of the crosslinked methacrylate(s) matrix and 70-90% by weight of one or more inorganic fillers having a mean particle size in the range of 0.01-2.0 microns, and the polymeric filler has a mean particle size of 20-50 microns. In yet another embodiment, the polymeric filler comprises 10-30% by weight of the crosslinked methacrylate(s) matrix and 70-90% by weight of one or more inorganic fillers having a mean particle size in the range of 0.01-2.0 microns, and the polymeric filler has a mean particle size of more than 20 microns. In one embodiment, the inorganic filler comprises a radiopaque filler. In a further embodiment, the radiopaque filler is selected from the group consisting of bariumaluminosilicate, bariumaluminoborosilicate, strontiumaluminosilicate, bariumfluoroaluminosilicate, strontiumfluoroaluminosilicate, strontiumzincfluoroaluminosilicate, zincaluminosilicate, ytterbium fluoride, yttrium fluoride, zirconia, zirconiumsilicate, and combinations thereof. In one embodiment, the polymeric filler is made of a polymeric filler dispersed in a polymeric matrix.

In one embodiment, none of the fillers are reactive towards the acidic polymerizable monomer or component (A).

The concentration of total fillers (E1+E2+E3) ranges from about 40% (w/w) to about 95% (w/w) of the dental restorative composition. In one embodiment, the concentration of total fillers (E1+E2+E3) ranges from about 60% (w/w) to about 90% (w/w) of the dental restorative composition. In one embodiment, the concentration of total fillers (E1+E2+E3) ranges from about 70% (w/w) to about 90% (w/w) of the dental restorative composition. The viscosity of the composition can be adjusted by varying the amount of total filler concentration. Low or medium viscosity paste (40-75% w/w total filler concentration) will be suitable as a base/liner or flowable composite filling material. High viscosity paste (70-95% w/w total filler concentration) will be suitable as a regular restorative filling material. In one embodiment, the total filler concentration is at least 65% by weight. In one embodiment, the total filler concentration is at least 70% by weight. In another embodiment, the total filler concentration is at least 75% by weight. In yet another embodiment, the total filler concentration is at least 80% by weight.

In one embodiment, the volumetric polymerization shrinkage of the self-adhering dental restorative composition is less than 6.0%. In another embodiment, the volumetric polymerization shrinkage of the self-adhering dental restorative composition is less than 5.0%. In another embodiment, the volumetric polymerization shrinkage of the self-adhering dental restorative composition is less than 4.5%. In another embodiment, the volumetric polymerization shrinkage of the dental self-adhering restorative composition is less than 3.5%. In yet another embodiment, the volumetric polymerization shrinkage of the dental self-adhering restorative composition is less than 3.0%.

In one embodiment, the shear bond strength of the dental restorative composition to both dentin and enamel are at least 10 MPa. In another embodiment, the shear bond strength of the dental restorative composition to both dentin and enamel are at least 12 MPa. In yet another embodiment, the shear bond strength of the dental restorative composition to both dentin and enamel are at least 15 MPa.

In one embodiment, the single-part, light-curable, self-adhering dental restorative composition of the current invention comprises: (A) one or more first polymerizable monomers having at least one phosphorus-containing acidic moiety and at least one ethylenically unsaturated group; (B) one or more second polymerizable monomers having a molecular weight of 100-250, at least one hydroxyl group, and at least one ethylenically unsaturated group; (C) one or more third polymerizable monomers having a molecular weight of 270-900, at least two ethylenically unsaturated groups and no acidic functional group; (D) at least one photo-initiator; (E1) one or more first fillers that are a polymeric filler having a mean particle size of more than 4.5 microns and less than 70 microns comprising 5-100% by weight of a crosslinked polymeric matrix and 0-95% by weight of at least one inorganic filler having a mean particle size in the range of 0.005-20 microns; (E2) one or more second fillers having a mean particle size of more than 0.25 microns, but no more than 4.5 microns; and (E3) one or more third fillers having a mean particle size of 0.005-0.25 microns. The weight ratio of (A+B):(C) ranges from 30:70 to 90:10, the concentration of component (A) in the restorative composition, excluding fillers, is in the range of 10-50% by weight, the concentration of component (B) in the restorative composition, excluding fillers, is in the range of 15-60% by weight, and the composition has a shear bond strength of at least 10 MPa to both dentin and enamel. All the descriptions and embodiments discussed in previous paragraphs concerning component (A), component (B), component (C), component (D), component (E1) when it is a polymeric filler, component (E2), and component (E3) of the single-part, light-curable, self-adhering dental restorative composition apply to this embodiment. In a further embodiment, component (E1) comprises 10-30% by weight of a crosslinked polymeric matrix and 70-90% by weight of the at least one inorganic filler. In yet a further embodiment, component (E1) comprises 10-30% by weight of a crosslinked poly(meth)acrylate polymeric matrix and 70-90% by weight of the at least one inorganic filler. In yet a still further embodiment, component (A) is a first polymerizable monomer selected from the group consisting of glyceryldi(meth)acrylate phosphate and bis{hydroxyethyl(meth)acrylate} phosphate, or a mixture thereof. In yet a still further embodiment, component (E1) includes one or more first fillers that are a polymeric filler having a mean particle size of more than 10 microns and less than 60 microns comprising 10-30% by weight of a crosslinked poly(meth)acrylate polymeric matrix and 70-90% by weight of at least one inorganic filler having a mean particle size in the range of 0.01-4.5 microns, the weight ratio of (A+B):(C) ranges from 30:70 to 80:20, and the concentration of component (A) in the restorative composition, excluding fillers, is in the range of 10-45% by weight. In further exemplary embodiments, the concentration of component (A) in the restorative composition, excluding fillers, is in the range of 15-40%, or in the range of 20-40%. In another exemplary embodiment, the first polymerizable monomer (A) is glyceryldi(meth)acrylate phosphate. In yet other exemplary embodiments, the weight ratio of (A+B):(C) ranges from 40:60 to 75:25, or from 45:55 to 75:25.

In one embodiment, the single-part, light-curable, self-adhering dental restorative composition of the current invention comprises: (A) a first polymerizable monomer selected from the group consisting of glyceryldi(meth)acrylate phosphate and bis{hydroxyethyl(meth)acrylate} phosphate, or a mixture thereof; (B) one or more second polymerizable monomers having a molecular weight of 100-250, at least one hydroxyl group, and at least one ethylenically unsaturated group; (C) one or more third polymerizable monomer having a molecular weight of 270-900, at least two ethylenically unsaturated groups and no acidic functional group; (D) at least one photo-initiator, (E1) one or more first fillers that are a polymeric filler having a mean particle size of more than 10 microns and less than 60 microns comprising 10-30% by weight of a crosslinked poly(meth)acrylate polymeric matrix and 70-90% by weight of at least one inorganic filler having a mean particle size in the range of 0.01-2.0 microns; (E2) one or more second fillers having a mean particle size of more than 0.25 microns, but no more than 2.0 microns; and (E3) one or more third fillers having a mean particle size of 0.01-0.25 microns. The weight ratio of (A+B):(C) ranges from 30:70 to 80:20, the concentration of component (A) in the restorative composition, excluding fillers, is in the range of 10-45% by weight, the concentration of component (B) in the restorative composition, excluding fillers, is in the range of 15-60% by weight, and the composition has a shear bond strength of at least 10 MPa to both dentin and enamel. All the descriptions and embodiments discussed in previous paragraphs concerning component (A), component (B), component (C), component (D), component (E1) when it is a polymeric filler, component (E2), and component (E3) of the single-part, light-curable, self-adhering dental restorative composition apply to this embodiment. In one embodiment, the concentration of component (A) in the restorative composition, excluding fillers, is in the range of 15-40%, or in the range of 20-40%. In one embodiment, the first polymerizable monomer (A) is glyceryldi(meth)acrylate phosphate. In one embodiment, the weight ratio of (A+B):(C) ranges from 40:60 to 75:25, or from 45:55 to 75:25.

The dental restorative composition may further comprise at least one ingredient selected from the group consisting of a colorant, a stabilizer, a UV absorber, a solvent, a fluoride-releasing compound, an antimicrobial additive, and a surfactant, or any mixture thereof. For the solvent, any solvent can be used. In one embodiment, the solvent is selected from the group consisting of ethanol, water, methanol, acetone, methyl ethyl ketone, isopropanol, and t-butanol, and any combination thereof. In another embodiment, the solvent is selected from the group consisting of ethanol, water, isopropanol, and t-butanol, and any combination thereof. In yet another embodiment, the solvent is water. In one embodiment, the concentration of solvent is in the range of 0% - 5% by weight. In another embodiment, the concentration of solvent is less than 1% by weight. In yet another embodiment, the composition is substantially free of any solvent or no solvent is added to the composition as a separate ingredient. The colorant is used to achieve desired shade and can be an inorganic pigment or an organic dye. The stabilizer is a polymerization inhibitor or retarder to improve the shelf stability of the adhesive composition. Most commonly used stabilizers include 2,6-di-(Cert-butyl)-4-methylphenol ("BHT") and 4-methoxyphenol ("MEHQ"). The UV absorber is used to improve the color stability of the adhesive composition upon exposure to UV light. An example of a UV absorber is 2-hydroxy-4-methoxybenzophenone ("UV-9"). A fluoride- releasing compound is any fluoride-containing substance that can release fluoride into saliva, water, or surrounding dentition. Examples of fluoride-releasing compounds include, but are not limited to, sodium fluoride, strontium fluoride, sodium hexafluorosilicate, zinc hexafluorosilicate, rare earth metal fluoride such as ytterbium fluoride, a salt formed by an amine and hydrofluoric acid, and a complex formed by an amine and $BF_3$, and combinations thereof. Examples of antimicrobial additives include, but are not limited to, benzalkonium chloride, iodoform, eugenol, zinc oxide, triclosan, alkyl 4-hydroxybenzoate, silicate glass powder containing silver and/or zinc, and zeolite powder containing silver and/or zinc ion(s). Useful antibacterial zeolites and their preparation are disclosed in U.S. Pat. Nos. 4,911,899 and 4,775,585, each of which is expressly incorporated by reference herein in its entirety.

A dispersant can be used to increase the filler loading in the self-adhering dental restorative composition to further minimize polymerization shrinkage. In one embodiment, the dispersant has a phosphate group. In another embodiment, the dispersant is polymerizable and has at least one ethylenically unsaturated group. Especially useful types of polymerizable dispersants and their preparation are disclosed in U.S. Pat. No. 6,359,090, which is expressly incorporated by reference herein in its entirety.

The current invention also discloses a restorative method of using the disclosed single-part, light-curable, self-adhering dental restorative composition. All the descriptions and embodiments discussed in previous paragraphs concerning the single-part, light-curable, self-adhering dental restorative composition apply to the restorative method of using the single-part, light-curable, self-adhering dental restorative composition. In one embodiment, the self-adhering dental restorative composition of the current invention can be used as a self-adhering dental filling material, a self-adhering base/liner/adhesive (meaning a base, a liner, or an adhesive) material, a self-adhering dental sealant, a self-adhering dental repair material, and/or a self-adhering undercut block-out material. In one embodiment, the method of using the self-adhering dental restorative composition of the current invention comprises: (i) applying the self-adhering dental restorative composition to tooth structure; and (ii) subsequently hardening the composition by light-curing the composition. In another embodiment, the method of using the self-adhering dental restorative composition of the current invention comprises: (i) applying the self-adhering dental restorative composition to tooth structure without first treating the tooth structure with an etchant, a primer and/or an adhesive;; and (ii) subsequently hardening the composition by light-curing the composition.

In one embodiment, the disclosed single-part, light-curable, self-adhering dental restorative composition is used as a filling material for filling a dental cavity without first treating the dental cavity with an etchant, a primer and/or an adhesive. The omission of the steps of treating the dental cavity with an etchant, a primer and an adhesive significantly simplifies the restorative procedures and would result in significant time savings for the dentists. In one embodiment, the cavity is filled with the disclosed self-adhering dental composition in bulk and the composition is then polymerized by light-curing. In another embodiment, the cavity is filled with the self-adhering dental composition in more than one increment and each increment is individually polymerized by light-curing.

In one embodiment, the disclosed single-part, light-curable, self-adhering dental restorative composition is used as a liner/base/adhesive for lining a dental cavity without first treating the dental cavity with an etchant, a primer and/or an adhesive. In this case, the self-adhering dental restorative composition is equivalent to a self-adhering adhesive. The lined dental cavity is then further filled with a dental composite filling material (e.g. Prodigy™ or Premise™ from Kerr Corporation, Orange, Calif., USA; Bisfill II™ from Bisco, Schumberger, Ill., USA) and the filling material is subsequently polymerized. In one embodiment, the liner/base/adhesive is polymerized or partially polymerized (e.g. by light-curing) before application of the dental composite filling material. In another embodiment, the liner/base/adhesive is not polymerized before application of the dental composite filling material. In one embodiment, the same self-adhering dental restorative composition of current invention can be used as the liner/base/adhesive material and also as the filling material.

In another embodiment, the disclosed single-part, light-curable, self-adhering dental restorative composition is used as a repair material for repairing damaged restorations without first treating the damaged restoration with a primer and/or an adhesive. The repair material is polymerized by light-curing after application. The damaged restorations can be a composite, ceramic, or metal-based restorations such as a filling material, an inlay, an onlay, a crown, or a core-buildup material. Before the inventive self-adhering restorative composition is applied to the bonding surface of the damaged restoration, the bonding surface of the damaged restoration can be optionally roughened with a dental bur (e.g. diamond bur, carbide bur or a polymeric bur) or by abrading with fine alumina particles (e.g. particle size of 25-100 microns) or other fine particles (air-abrasion) to further enhance the adhesion. Examples of ceramic restorative materials include porcelains, feldspathic porcelains, aluminous porcelains, lithium disilicate reinforced ceramic material such as IPS Eris® (Vivadent, N.Y.), leucite reinforced ceramic materials such as IPS Empress® and ProCAD® (Vivadent, N.Y.), glass infiltrated magnesia aluminate spinell, glass-infiltrated alumina, and glass-infiltrated zirconia. Examples of metal-based restorative materials include metal oxide, non-precious metal alloy, and precious metal alloy. Examples of metal oxide restorative materials include, but are not limited to zirconia, yttrium stabilized zirconia, and alumina. Example of zirconia-based restorative materials include Lava® (3M ESPE, MN), Cercon® (Dentsply, Del.), and Porcera® Zirconia (Nobel Biocare USA, CA). Examples of alumina-based restorative materials include, but are not limited to, Vita® in-Ceram® alumina (Vident, Calif.) and Porcera® alumina (Nobel Biocare USA, CA). Examples of non-precious metal alloy include, but are not limited to, Rexillium III® (a nickel-chromium alloy, Pentron Alloys, CA). Examples of precious metal alloy include, but are not limited to, gold alloy, and gold-platinum alloy. Examples of composite restorative material include, but are not limited to, Premise™ (Kerr, CA), Prodigy™ (Kerr, CA), belleGlass® NG (Kerr, CA), and Sinfony™ (3M ESPE, MN).

In one embodiment, the disclosed single-part, light-curable, self-adhering dental restorative composition is used as a dental sealant for sealing/filling dental pits and fissures without first treating the dental cavity with an etchant, a primer and/or an adhesive.

In another embodiment, the disclosed single-part, light-curable, self-adhering dental restorative composition is used as a block-out material to block out any undercut of a cavity or dental preparation without first treating the dental cavity/preparation with an etchant, a primer and/or an adhesive.

The current invention also discloses a dental restorative kit comprising the disclosed single-part, light-curable, self-adhering dental restorative composition and an instruction for using the composition. The dental restorative kit does not include a dental primer or adhesive. All the descriptions and embodiments discussed in previous paragraphs concerning the single-part, light-curable, self-adhering dental restorative composition apply to above single-part, light-curable, self-adhering dental restorative composition in the dental restorative kit.

In one embodiment, the instructions teach a method of filling a dental cavity with the disclosed self-adhering dental composition without first treating the dental cavity with an etchant, a primer, and/or an adhesive. In another embodiment, the instructions teach a method of lining a dental cavity with the disclosed self-adhering dental composition without first treating the dental cavity with an etchant, a primer, and/or an adhesive. In another embodiment, the instructions teach a method of repairing a damaged restoration with the disclosed self-adhering dental composition without first treating the damaged restoration with a primer, and/or an adhesive.

EXAMPLES

Compressive Strength (CS) Test

The specimens were prepared by condensing the dental restorative composition, in paste form (referred to simply as "the paste"), into a stainless-steel mold with a dimension of 4mm (diameter)×3 mm (height), and then photo-curing the paste with a Demetron Optilux™ 501 curing light (Kerr Corp.) for 30-seconds from each side. The cured disk was removed from the mold and conditioned in 37° C. water for 24 hours before subjecting to mechanical testing on an Instron Universal Tester (Model 4202) in compression mode with a crosshead speed of 0.50 mm/minute. The peak load at which the specimen broke was used to calculate the CS expressed in MPa unit. Six specimens were tested for each formula.

Diametral Tensile Strength (DTS) Test

The specimens were prepared by condensing the paste into a stainless-steel mold with a dimension of 6mm (diameter)×3mm (height), and then photo-curing the paste with a Demetron Optilux™ 501 curing light (Kerr Corp.) for 30-seconds from each side. The cured disk was removed from the mold and conditioned in 37° C. water for 24 hours before subjecting to mechanical testing on an Instron Universal Tester (Model 4202) in compression mode with a crosshead speed of 10 mm/minute. The load was applied in the diameter direction in compression mode. The peak load at which the specimen broke was used to calculate the DTS expressed in MPa unit. Six specimens were tested for each formula.

Flexural Strength (FS) and Young's Modulus (E) Tests

FS and E were measured from the same flexural test according to ISO 4049 standard. The specimens were prepared by condensing the paste into a stainless-steel mold with a dimension of 2mm×2mm×25mm, and then photo-cured from both sides. The cured disk was removed from the mold and conditioned in 37° C. water for 24 hours before subjecting to mechanical testing on an Instron Universal Tester (Model 4202) in 3-point bending mode with a crosshead speed of 0.5 mm/minute. The peak load at which the specimen broke was used to calculate the FS expressed in MPa unit. E was obtained from the slope of the stress-strain curve in the initial linear region. Five specimens were tested for each formula.

The Volumetric Polymerization Shrinkage (VPS)

VPS was calculated based on the measured densities of the material before and after light-curing with the Demetron Optilux™ 501 curing light for 60 seconds (30 seconds each side). The density was measured using the buoyancy method in de-ionized water.

Shear Bond Strength (SBS) to Enamel

The enamel bond strength test was conducted as follows: Bovine enamel specimens were embedded in cold-cure acrylics. A set of 6 specimens was prepared for each group. The enamel surface was then prepared with a fine diamond bur to create a new surface, and the surface was cleaned by rinsing with water and dried with compressed air from a dental air syringe for about 3 seconds. Without etching the enamel surface with an etchant or conditioning the enamel surface with a primer/adhesive, the bovine enamel surface was then held securely by a bonding jig (Ultradent Inc., UT) with a cylindrical mold ($\Phi$=2.38 mm) The self-adhering restorative composition was condensed inside the mold, and light-cured for 30 seconds using the Demetron Optilux™ 501 (Kerr, CA) dental curing light. After conditioning in 37° C. water for 20-24 hours, the bond strength was tested on an Instron mechanical tester (Model 4467, Instron, MA) in shear mode using a notched (semi-circular) edge at a crosshead speed of 1.0 mm/min The SBS to Enamel was calculated by dividing the peak load by the bonding area and expressed in MPa.

Shear Bond Strength (SBS) to Dentin

Dentin bond strength test was conducted according to following method: Extracted human teeth were embedded in cold-cure acrylics. A set of six specimens was prepared for each group. A low speed diamond saw was used to remove the crown and expose the occlusal dentin. The dentin substrates were polished with 240-grit and subsequently 600-grit SiC paper, rinsed thoroughly with water, and air dried briefly. Without etching the dentin surface with an etchant or conditioning the dentin surface with a primer/adhesive, the dentin surface was then held securely by a bonding jig (Ultradent Inc., UT) with a cylindrical mold ($\Phi$=2.38 mm) The self-adhering restorative composition was condensed inside the mold, and light-cured for 30 seconds using an Optilux™ 501 (Kerr, CA) dental curing light. After conditioning in 37° C. water for 20-24 hours, the bond strength was tested on an Instron mechanical tester (Model 4467, Instron, MA) in shear mode using a notched (semi-circular) edge at a crosshead speed of 1.0 mm/min The SBS to Dentin was calculated by dividing the peak load by the bonding area and expressed in MPa.

In this example, neither the enamel surface nor the dentin surface was etched with an etchant or pre-conditioned with an adhesive before bonding with the self-adhering restorative composition. The self-adhesiveness of the composition toward both dentin and enamel was clearly demonstrated.

Abbreviations for materials used in all examples:

Bis-GMA: 2,2-bis [4-(2-hydroxy-3-methacryloylpropoxy)-phenyl]-propane CQ: camphorquinone.
ETMPTA-3EO: ethoxylated trimethylolpropane triacrylate with 3 moles of ethylene oxide
EBPADMA-6EO: ethoxylated bisphenol A dimethacrylate with 6 moles of ethylene oxide,
GDM: glyceryldimethacrylate
GDM-P: glyceryldimethacrylate phosphate or glyceryldimethacrylate dihydrogen phosphate
HEMA: hydroxyethyl methacrylate
MEHQ: 4-methoxyphenol
4-MET: 4-methacryloxyethyltrimellitic acid
ODMAB: 2-ethylhexyl 4-(N,N-dimethylamino) benzoate
PF: A polymeric filler with a mean particle size of 35 microns comprising 19.4% by weight of crosslinked methacrylates and 80.6% by weight of inorganic fillers. The crosslinked methacrylates are a polymerized mixture of Bis-GMA, TEGDMA, and EBPADMA-2.5EO with benzoyl peroxide heat-cure initiator. The inorganic fillers comprise fumed silica (0.04 micron), Bariumaluminoborosilicate (0.7 micron) and Ytterbium fluoride (aggregated 40nm Ytterbium fluoride and the aggregated particle has a mean particle size of 0.7 microns).
ST-OX-50: fumed silica OX-50 surface treated with Y-methacryloyloxypropyltrimethoxysilane.
ST-BAS-1: Bariumaluminoborosilicate filler that has a mean particle size of 1 micron and its surface was treated with Y-methacryloyloxypropyltrimethoxysilane.
ST-BAS-4: Bariumaluminoborosilicate filler that has a mean particle size of 4 micron and its surface was treated with Y-methacryloyloxypropyltrimethoxysilane.
ST-BAS-10: Bariumaluminoborosilicate filler that has a mean particle size of 10 micron and its surface was treated with Y-methacryloyloxypropyltrimethoxysilane.
ST-BAS-0.4: Bariumaluminoborosilicate filler that has a mean particle size of 0.4 micron and its surface was treated with Y-methacryloyloxypropyltrimethoxysilane.
TS-530: Surface treated fumed silica or colloidal silica sold by Cabot Corp.
UDMA: reaction product of 2-hydroxyethyl methacrylate with 2,4,4-trimethylhexane diisocyanate
UV-9: 2-hydroxy-4-methoxybenzophenone
YbF3: Ytterbium fluoride (aggregated 40 nm Ytterbium fluoride particles and the aggregated particles have a mean particle size of 0.6 microns).

In all the examples for making the single-part, light-curable, self-adhering restorative material compositions, a homogeneous resin mixture was made first by mixing all resins with initiators and additives that are soluble in the resin mixture. Then the resin mixture was further blended together with various fillers to make the restorative composition, in paste form. Unless otherwise indicated, all parts and percentages are by weight in all examples.

The compositions used for all examples and their testing results are listed in Table 1.

TABLE 1

Self-adhering Dental Restorative Compositions

| | A (wt. %) | B (wt. %) | C (wt. %) | D (wt. %) | E (wt. %) | F (wt. %) | G (wt. %) | H (wt. %) | I (wt. %) |
|---|---|---|---|---|---|---|---|---|---|
| GDM-P | 5.49 | 8.81 | 9.40 | 5.87 | 6.02 | 6.17 | 6.05 | 7.33 | 4.84 |
| HEMA | 8.24 | 8.81 | 9.40 | 5.87 | 6.02 | 6.17 | 6.05 | 4.07 | 6.05 |
| 4-MET | | | | | | | | | 1.17 |
| GDM | 4.12 | 2.94 | 3.13 | 1.96 | | 2.06 | 2.02 | 2.04 | 2.02 |
| ETMPTA-3EO | 1.37 | | | | | | | | |
| EBPADMA-6EO | | | | | 4.01 | | | | |
| Bis-GMA | 8.24 | 2.94 | 3.13 | 1.96 | 2.01 | 2.06 | 2.02 | 2.04 | 2.02 |
| UDMA | | 5.87 | 6.26 | 3.92 | 2.01 | 4.11 | 4.03 | 4.88 | 4.07 |
| UV-9 | | 0.29 | 0.31 | 0.20 | 0.20 | 0.21 | 0.20 | 0.20 | 0.20 |
| ODMAB | 0.27 | 0.23 | 0.25 | 0.16 | 0.16 | 0.16 | 0.16 | 0.16 | 0.16 |
| CQ | 0.08 | 0.09 | 0.09 | 0.06 | 0.06 | 0.06 | 0.06 | 0.06 | 0.06 |
| MEHQ | 0.02 | 0.02 | 0.02 | 0.01 | 0.01 | 0.01 | 0.01 | 0.01 | 0.01 |
| PF | | 49.00 | 33.00 | 28.00 | 28.00 | 28.00 | 28.00 | 27.72 | 28.00 |
| ST-BAS-1 | 46.40 | 20.00 | | 38.13 | 22.50 | 20.00 | 29.40 | 29.70 | 29.40 |
| ST-BAS-0.4 | | | 34.00 | | | | | | |
| ST-BAS-4 | | | | | 18.00 | 18.00 | 11.00 | 10.89 | 11.00 |
| ST-BAS-10 | 20.86 | | | | | | | | |
| YbF3 | | | | 10.00 | 10.00 | 10.00 | 10.00 | 9.90 | 10.00 |
| ST-OX-50 | 1.82 | | | 2.87 | | | | | |
| TS-530 | 3.09 | 1.00 | 1.00 | 1.00 | 1.00 | 3.00 | 1.00 | 0.99 | 1.00 |
| TOTAL, % | 100.00 | 100.00 | 100.00 | 100.00 | 100.00 | 100.00 | 100.00 | 100.00 | 100.00 |
| TESTING RESULTS | | | | | | | | | |
| SBS to Dentin, MPa (s.d.) | 24.4 (8.7) | 22.0 (5.4) | 26.6 (6.3) | 21.2 (2.4) | 20.7 (3.6) | 21.9 (2.2) | 21.1 (2.0) | 18.3 (1.7) | 23.7 (4.0) |
| SBS to Enamel, MPa (s.d.) | N/A | 23.4 (6.0) | 22.5 (5.7) | 21.0 (1.9) | 25.1 (1.2) | 25.8 (3.2) | 25.6 (1.5) | 20.5 (1.6) | 24.9 (3.1) |
| Compressive Strength, MPa (s.d.) | N/A | N/A | N/A | 375.4 (40) | 265.8 (16) | 385.3 (9) | 381.8 (27) | N/A | 375.8 (21) |
| Diametral Tensile Strength, MPa (s.d.) | N/A | N/A | N/A | 53.5 (2.5) | 53.0 (4.5) | 56.6 (3.5) | 57.5 (5.5) | N/A | 52.4 (8.6) |
| Flexural Strength, MPa (s.d.) | N/A | N/A | N/A | 116.9 (7) | N/A | 118.9 (12) | 113.4 (13.1) | N/A | 108.4 (5.3) |
| Volume Shrinkage, (s.d.) | N/A | N/A | N/A | N/A | 3.32 (0.17) | N/A | 3.36 (0.32) | N/A | N/A |

All self-adhering restorative compositions exhibited good mechanical strengths and bond strengths.

Much simplified restorative procedures and significant time savings will result when the inventive composition and method is used as a self-adhering dental filling material, a self-adhering dental base/liner, or a self-adhering dental repair material. As a result, the steps of applying an etchant, a primer, and an adhesive to tooth structure are omitted. The self-adhering restorative composition is bonded directly to tooth surface either as a base/liner, a filling material, or a repairing material.

The above examples illustrate how the current invention is applied and should not limit the scope of the invention.

What is claimed is:

1. A single-part, light-curable, self-adhering dental restorative composition consisting essentially of:
    (A) one or more first polymerizable monomers consisting of (A1) a first phosphate selected from the group consisting of hydroxyethyl (meth)acrylate phosphate, hydroxypropyl (meth)acrylate phosphate, hydroxybutyl (meth)acrylate phosphate, dipentaerythritol penta (meth)acrylate phosphate, pentaerythritol tri(meth) acrylate phosphate, phenyl (meth)acryloxyethyl phosphate, and a combination thereof, and optionally (A2) a second phosphate selected from the group consisting of glyceryldi(meth)acrylate phosphate, bis {hydroxyethyl (meth)acrylate} phosphate, and a combination thereof;
    (B) one or more second polymerizable monomers having a molecular weight of 100-250, at least one hydroxyl group, and at least one ethylenically unsaturated group;
    (C) one or more third polymerizable monomers having a molecular weight of 270-900, at least two ethylenically unsaturated groups and no acidic functional group;
    (D) a photo-initiator system having at least one photo-initiator;
    (E) one or more fillers each having a mean particle size of more than 0.005 microns and less than 70 microns;
    (F) optionally one or more ingredients selected from the group consisting of: a colorant, a stabilizer, a UV absorber, a solvent, a fluoride-releasing compound, an antimicrobial additive, and a surfactant;
    wherein the weight ratio of (A+B) : (C) ranges from 30:70 to 90:10; and
    the composition has a shear bond strength of at least 10MPa to both dentin and enamel after being light-cured.

2. The self-adhering dental restorative composition of claim 1 wherein the weight ratio of (A+B) : (C) ranges from 45:55 to 75:25.

3. The self-adhering dental restorative composition of claim 1 wherein the concentration of component (A) in the restorative composition, excluding fillers, is in the range of 15-40% by weight, and the concentration of component (B) in the restorative composition, excluding fillers, is in the range of 20-50% by weight.

4. The self-adhering dental restorative composition of claim 1 wherein the ethylenically unsaturated groups in (B) and (C) are each selected from the group consisting of acrylate, methacrylate, acrylamide, methacrylamide, and vinyl groups, or any combination thereof.

5. The self-adhering dental restorative composition of claim 1 wherein the one or more first polymerizable monomers (A) includes at least one second phosphate (A2).

6. The self-adhering dental restorative composition of claim 5 wherein the concentration of component (A) in the restorative composition, excluding fillers, is in the range of 10-50% by weight, and the concentration of component (B) in the restorative composition, excluding fillers, is in the range of 15-60% by weight.

7. The self-adhering dental restorative composition of claim 1 wherein the one or more fillers are non-reactive towards the one or more first polymerizable monomers.

8. The self-adhering dental restorative composition of claim 1 wherein component (E) comprises: (E1) one or more first fillers having a mean particle size of more than 4.5 microns and less than 70 microns; (E2) one or more second fillers having a mean particle size of more than 0.25microns, but no more than 4.5 microns; and (E3) one or more third fillers having a mean particle size of 0.005-0.25 microns.

9. The self-adhering dental restorative composition of claim 8 wherein the one or more first fillers (E1) have a mean particle size of more than 10 microns.

10. The self-adhering dental restorative composition of claim 8 wherein the one or more first fillers (E1) are a polymeric filler comprising 5-100% by weight of a polymeric matrix and 0-95% by weight of at least one inorganic filler.

11. The self-adhering dental restorative composition of claim 10 wherein the polymeric filler comprises 10-50% by weight of the polymeric matrix and 50-90% by weight of the at least one inorganic filler.

12. The self-adhering dental restorative composition of claim 11 wherein the polymeric matrix comprises crosslinked (meth)acrylate(s), and wherein the mean particle size of the inorganic filler(s) is in the range of 0.005-20 microns.

13. The self-adhering dental restorative composition of claim 12 wherein the mean particle size of the inorganic filler(s) is in the range of 0.01-4.5 microns.

14. The self-adhering dental restorative composition of claim 8 wherein the one or more second fillers (E2) have a mean particle size of 0.3-2.0 microns.

15. The self-adhering dental restorative composition of claim 1 wherein the total concentration of the one or more fillers in the restorative composition is in the range from 40-95% by weight.

16. The self-adhering dental restorative composition of claim 1 wherein the shear bond strength is at least 12 MPa to both dentin and enamel.

17. A method of using the self-adhering dental restorative composition of claim 1 comprises:
    (i) applying the self-adhering dental restorative composition to tooth structure without first treating the tooth structure with an etchant, a primer and/or an adhesive; and
    (ii) subsequently hardening the composition by light-curing the composition.

18. A dental restorative kit comprising the self-adhering dental restorative composition of claim 1 and an instruction of how to use the composition, wherein the instruction teaches to restore a dental cavity by first applying the single-part, light-curable, self-adhering dental restorative composition directly to the dental cavity without first treating the dental cavity with an etchant, a primer and/or an adhesive.

19. A single-part, light-curable, self-adhering dental restorative composition consisting essentially of:
    (A) one or more first polymerizable monomers consisting of (A1) a first phosphate selected from the group consisting of hydroxyethyl (meth)acrylate phosphate, hydroxypropyl (meth)acrylate phosphate, hydroxybutyl (meth)acrylate phosphate, dipentaerythritol penta (meth)acrylate phosphate, pentaerythritol tri(meth) acrylate phosphate, phenyl (meth)acryloxyethyl phosphate, and a combination thereof, and optionally (A2) a second phosphate selected from the group consisting of glyceryldi(meth)acrylate phosphate, bis {hydroxyethyl (meth)acrylate} phosphate, and a combination thereof;
(B) one or more second polymerizable monomers having a molecular weight of 100-250, at least one hydroxyl group, and at least one ethylenically unsaturated group;
(C) one or more third polymerizable monomers having a molecular weight of 270-900, at least two ethylenically unsaturated groups and no acidic functional group;
(D) a photo-initiator system having at least one photo-initiator;
(E1) one or more first fillers that are a polymeric filler having a mean particle size of more than 4.5 microns and less than 70 microns comprising 5-100% by weight of a crosslinked polymeric matrix and 0-95% by weight of at least one inorganic filler having a mean particle size in the range of 0.005-20 microns;
(E2) one or more second fillers having a mean particle size of more than 0.25microns, but no more than 4.5 microns; and
(E3) one or more third fillers having a mean particle size of 0.005-0.25microns;
(F) optionally one or more ingredients selected from the group consisting of: a colorant, a stabilizer, a UV absorber, a solvent, a fluoride-releasing compound, an antimicrobial additive, and a surfactant;
wherein the weight ratio of (A+B) : (C) ranges from 30:70 to 90:10;
the concentration of component (A) in the restorative composition, excluding fillers, is in the range of 10-50% by weight;
the concentration of component (B) in the restorative composition, excluding fillers, is in the range of 15-60% by weight; and
the composition has a shear bond strength of at least 10MPa to both dentin and enamel after being light-cured.

20. The self-adhering dental restorative composition of claim 19 wherein:
(E1) the polymeric filler has a mean particle size of more than 10 microns and less than 60 microns comprising 10-30% by weight of a crosslinked poly(meth)acrylate polymeric matrix and 70-90% by weight of at least one inorganic filler having a mean particle size in the range of 0.01-4.5microns;
the weight ratio of (A+B) : (C) ranges from 30:70 to 80:20; and
the concentration of component (A) in the restorative composition, excluding fillers, is in the range of 10-45% by weight.

21. The self-adhering dental restorative composition of claim 20 wherein:
(E1) the at least one inorganic filler has a mean particle size in the range of 0.01-2.0microns;
(E2) the one or more second fillers have a mean particle size of more than 0.25microns, but no more than 2.0 microns; and
(E3) the one or more third fillers have a mean particle size of 0.01-0.25microns.

22. The single-part, light-curable, self-adhering dental restorative composition of claim 19 wherein the one or more first polymerizable monomers (A) includes at least one second phosphate (A2).

23. A method of using the self-adhering dental restorative composition of claim 19 comprises:
(i) applying the self-adhering dental restorative composition to tooth structure without first treating the tooth structure with an etchant, a primer and/or an adhesive; and
(ii) subsequently hardening the composition by light-curing the composition.

\* \* \* \* \*

UNITED STATES PATENT AND TRADEMARK OFFICE
CERTIFICATE OF CORRECTION

| | |
|---|---|
| PATENT NO. | : 8,162,665 B2 |
| APPLICATION NO. | : 13/110253 |
| DATED | : April 24, 2012 |
| INVENTOR(S) | : Xuejun Qian |

It is certified that error appears in the above-identified patent and that said Letters Patent is hereby corrected as shown below:

Col. 14, line 32, "($\Phi$=2.38 mm)" should read --($\Phi$=2.38 mm).--

Col. 14, line 52, "($\Phi$=2.38 mm)" should read --($\Phi$=2.38 mm).--

Col. 14, line 59, "1.0 mm/min" should read --1.0 mm/min.--

Signed and Sealed this
Tenth Day of July, 2012

David J. Kappos
*Director of the United States Patent and Trademark Office*